(12) United States Patent
Desmet et al.

(10) Patent No.: US 8,278,073 B2
(45) Date of Patent: Oct. 2, 2012

(54) LACTOSE PHOSPHORYLASE ENZYMES

(75) Inventors: Tom Desmet, Nevele (BE); Manu De Groeve, Vlierzele (BE); Wim Soetaert, Lovendegem (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 12/735,023

(22) PCT Filed: Dec. 19, 2008

(86) PCT No.: PCT/EP2008/068076
§ 371 (c)(1),
(2), (4) Date: Sep. 2, 2010

(87) PCT Pub. No.: WO2009/080774
PCT Pub. Date: Jul. 2, 2009

(65) Prior Publication Data
US 2011/0008849 A1   Jan. 13, 2011

(30) Foreign Application Priority Data
Dec. 20, 2007  (EP) .................................. 07150211

(51) Int. Cl.
*C12N 9/10*  (2006.01)
(52) U.S. Cl. ........ 435/100; 435/193; 435/105; 530/350; 536/23.1

(58) Field of Classification Search .................. None
See application file for complete search history.

(56) References Cited

U.S. PATENT DOCUMENTS 5,849,529 A * 12/1998 Hayashi et al. ............. 435/69.1
6,764,841 B2  7/2004 Igarashi et al.

FOREIGN PATENT DOCUMENTS

| EP | 0 553 297 | 1/1995 |
| JP | 9224691 | 9/1997 |
| WO | WO 92/09612 | 6/1992 |
| WO | WO 2005 056786 | 6/2005 |
| WO | WO 2009/080774 A1 | 7/2009 |

OTHER PUBLICATIONS

Sasaki et al., Purification and properties of Cellvibrio gilvus cellobiose phosphorylase. Biochem. J., 1983, pp. 803-807, vol. 209.
DATABASE UniProt [Online] May 15, 2007. Putative cellobiose phosphorylase. XP002477663 retrieved from EBI accession No. UNIPROT:A4Q9G7, Database accession No. A4Q9G1.
Database UniProt [Online] Mar. 1, 2002. Cellobiose phosphorylase. XP002477664 retrieved from EBI accession No. UNIPROT:Q8VP44, Database accession No. Q8VP44.
DATABASE UniProt [Online] Oct. 1, 2003, SubName: Full=Cellobiose phosphorylase. XP002517134 retrieved from EBI accession No. UNIPROT:Q7WTR6, Database accession No. Q7WTR6.

* cited by examiner

Primary Examiner — Hope Robinson
(74) Attorney, Agent, or Firm — TraskBritt

(57) ABSTRACT

The present invention relates to novel lactose phosphorylase enzymes and the uses thereof. More specifically, the invention relates to lactose phosphorylase enzymes created by mutation of a cellobiose phosphorylase from *Cellulomonas uda*. By introducing mutations in this enzyme, the activity can be switched from cellobiose phosphorylase into lactose phosphorylase.

8 Claims, No Drawings

SEQUENCE LISTING

```
<160> NUMBER OF SEQ ID NOS: 10

<210> SEQ ID NO 1
<211> LENGTH: 822
<212> TYPE: PRT
<213> ORGANISM: Cellulomonas uda

<400> SEQUENCE: 1

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160

Gln Thr Asn Tyr Gln Arg Asn Leu Ser Ile Gly Glu Val Glu Val Glu
                165                 170                 175

Gln Glu Ser Pro His Gly Ser Ala Ile Tyr His Arg Thr Glu Tyr Arg
            180                 185                 190

Glu Arg Arg Asp His Tyr Ala Val Phe Ala Val Asn Thr Gln Ala Glu
        195                 200                 205

Gly Phe Asp Thr Asp Arg Asp Thr Phe Val Gly Ala Tyr Asn Ser Leu
    210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Asp Ala Lys Gln Val Val Asn Lys
        275                 280                 285
```

-continued

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                    325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                    405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                    485                 490                 495

Phe Ser Thr Thr Pro Gly Glu Ser Phe Gln Thr Thr Glu Asn Gln Ala
            500                 505                 510

Gly Gly Val Ala Glu Ser Thr Phe Ile Ala Ala Gln Phe Val Leu Tyr
        515                 520                 525

Gly Glu Gln Tyr Ala Glu Leu Ala Ala Arg Arg Gly Leu Ala Asp Val
530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                    565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
        595                 600                 605

Pro Gln Asp Thr Asp Ala Pro Ala Ile Lys Ala Leu Asp Ser Val Asn
610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                    645                 650                 655

Tyr Lys Glu Asn Gly Gly Ile Phe Cys His Asn Asn Pro Trp Val Ile
            660                 665                 670

Ile Ala Glu Thr Val Val Gly Arg Gly Gly Arg Ala Phe Asp Tyr Tyr
        675                 680                 685

Lys Arg Ile Thr Pro Ala Tyr Arg Glu Asp Ile Ser Asp Val His Arg
690                 695                 700

Leu Glu Pro Tyr Val Tyr Ala Gln Met Ile Ala Gly Lys Glu Ala Val

```
                    705                 710                 715                 720
Arg His Gly Glu Ala Lys Asn Ser Trp Leu Thr Gly Thr Ala Ala Trp
                    725                 730                 735

Asn Phe Val Thr Val Ser Gln Tyr Leu Leu Gly Val Arg Pro Glu Tyr
                    740                 745                 750

Asp Gly Leu Val Val Asp Pro Gln Ile Gly Pro Asp Val Pro Ser Phe
                    755                 760                 765

Thr Val Thr Arg Val Ala Arg Gly Ala Thr Tyr Glu Ile Thr Val Thr
                    770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                    805                 810                 815

Arg Val Asp Val Thr Leu
                    820

<210> SEQ ID NO 2
<211> LENGTH: 822
<212> TYPE: PRT
<213> ORGANISM: Artificial
<220> FEATURE:
<223> OTHER INFORMATION: Mutant sequence 1

<400> SEQUENCE: 2

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
                    20                  25                  30

Phe Phe Ser Leu Leu Ser His Gln Ala Gly Gly Tyr Ser Phe Tyr Arg
                35                  40                  45

Asp Ala Lys Met Arg Arg Leu Thr Arg Tyr Arg Tyr Asn Asn Ile Pro
            50                  55                  60

Ala Asp Ala Gly Gly Arg Tyr Leu Tyr Val Asn Asp Gly Gly Asp Val
65              70                  75                  80

Trp Thr Pro Ser Trp Leu Pro Val Lys Ala Asp Leu Asp His Phe Glu
                    85                  90                  95

Ala Arg His Gly Leu Gly Tyr Ser Thr Ile Thr Gly Glu Arg Asn Gly
                100                 105                 110

Val Arg Val Glu Thr Leu Phe Phe Val Pro Val Gly Glu Asn Ala Glu
            115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Gln Thr Asn Tyr Gln Arg Asn Leu Ser Ile Gly Glu Val Glu Val Glu
                165                 170                 175

Gln Glu Ser Pro His Gly Ser Ala Ile Tyr His Arg Thr Glu Tyr Arg
                180                 185                 190

Glu Arg Arg Asp His Tyr Ala Val Phe Ala Val Asn Thr Gln Ala Glu
            195                 200                 205

Gly Phe Asp Thr Asp Arg Asp Thr Phe Val Gly Ala Tyr Asn Ser Leu
        210                 215                 220

Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255
```

-continued

Pro Gly Glu Ser Arg Glu Leu Val Tyr Val Leu Gly Tyr Val Glu Asn
    260                 265                 270

Pro Asp Glu Glu Lys Trp Ala Asp Ala Lys Gln Val Val Asn Lys
    275                 280                 285

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
                340                 345                 350

Ala Ser Phe Phe Glu Thr Gly Ile Gly Arg Gly Met Gly Phe Arg Asp
            355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
                420                 425                 430

Ala Tyr Ile Lys Glu Thr Gly Asp Phe Ser Ile Leu Asp Glu Pro Val
            435                 440                 445

Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Ala Glu Asn Gln Ala
                500                 505                 510

Gly Gly Val Ala Glu Ser Thr Phe Ile Ala Ala Gln Phe Val Leu Tyr
            515                 520                 525

Gly Glu Gln Tyr Ala Glu Leu Ala Ala Arg Arg Gly Leu Ala Asp Val
    530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
                580                 585                 590

Glu Pro Gln Gly Phe Ala Val Met Ala Gly Val Gly Val Gly Glu Gly
            595                 600                 605

Pro Gln Asp Thr Asp Ala Pro Ala Ile Lys Ala Leu Asp Ser Val Asn
    610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Thr Asn Pro Trp Val Ile
                660                 665                 670

Ile Ala Glu Thr Val Val Gly Arg Gly Gly Arg Ala Phe Asp Tyr Tyr

```
                675                 680                 685
Lys Arg Ile Thr Pro Ala Tyr Arg Glu Asp Ile Ser Asp Val His Arg
            690                 695                 700

Leu Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
            770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 3
<211> LENGTH: 822
<212> TYPE: PRT
<213> ORGANISM: Artificial
<220> FEATURE:
<223> OTHER INFORMATION: Mutant sequence 2

<400> SEQUENCE: 3

Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Arg Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
130                 135                 140

Thr Leu Phe Ser Phe Val Glu Phe Cys Leu Trp Asn Ala Gln Asp Asp
145                 150                 155                 160

Gln Thr Asn Tyr Gln Arg Asn Leu Ser Ile Gly Glu Val Glu Val Glu
                165                 170                 175

Gln Glu Ser Pro His Gly Ser Ala Ile Tyr His Arg Thr Glu Tyr Arg
            180                 185                 190

Glu Arg Arg Asp His Tyr Ala Val Phe Ala Val Asn Thr Gln Ala Glu
        195                 200                 205

Gly Phe Asp Thr Asp Arg Asp Thr Phe Val Gly Ala Tyr Asn Ser Leu
    210                 215                 220
```

```
Gly Glu Ala Ala Val Pro Leu Lys Gly Glu Ser Ala Asn Ser Val Ala
225                 230                 235                 240

Ser Gly Trp Tyr Pro Ile Gly Ser His Ser Val Ala Val Ser Leu Ala
                245                 250                 255

Pro Gly Glu Ser Arg Glu Leu Val Tyr Val Leu Gly Tyr Val Glu Asn
            260                 265                 270

Pro Asp Glu Glu Lys Trp Ala Asp Ala Lys Gln Val Val Asn Lys
        275                 280                 285

Glu Arg Ala His Ala Leu Leu Ser Arg Phe Ala Thr Ser Glu Gln Thr
    290                 295                 300

Asp Ala Ala Phe Ala Ala Leu Lys Asp Tyr Trp Thr Asp Leu Leu Ser
305                 310                 315                 320

Thr Tyr Ser Val Ser Ser Asn Asp Glu Lys Leu Asp Arg Met Val Asn
                325                 330                 335

Ile Trp Asn Gln Tyr Gln Cys Met Val Thr Phe Asn Met Ser Arg Ser
            340                 345                 350

Ala Ser Phe Phe Glu Thr Gly Ile Gly Arg Gly Met Gly Phe Arg Asp
        355                 360                 365

Ser Asn Gln Asp Leu Leu Gly Phe Val His Leu Ile Pro Glu Arg Ala
    370                 375                 380

Arg Glu Arg Ile Ile Asp Ile Ala Ser Thr Gln Phe Ala Asp Gly Ser
385                 390                 395                 400

Ala Tyr His Gln Tyr Gln Pro Leu Thr Lys Arg Gly Asn Asn Asp Ile
                405                 410                 415

Gly Ser Gly Phe Asn Asp Asp Pro Leu Trp Leu Ile Ala Gly Thr Ala
            420                 425                 430

Ala Tyr Ile Lys Glu Thr Gly Asp Phe Ser Ile Leu Asp Glu Pro Val
        435                 440                 445

Pro Phe Asp Asn Glu Pro Gly Ser Glu Val Pro Leu Phe Glu His Leu
    450                 455                 460

Thr Arg Ser Phe Glu Phe Thr Val Thr His Arg Gly Pro His Gly Leu
465                 470                 475                 480

Pro Leu Ile Gly Arg Ala Asp Trp Asn Asp Cys Leu Asn Leu Asn Cys
                485                 490                 495

Phe Ser Thr Thr Pro Gly Glu Ser Phe Gln Thr Ile Glu Asn Gln Ala
            500                 505                 510

Gly Gly Val Ala Glu Ser Thr Phe Ile Ala Ala Gln Phe Val Leu Tyr
        515                 520                 525

Gly Glu Gln Tyr Ala Glu Leu Ala Ala Arg Arg Gly Leu Ala Asp Val
    530                 535                 540

Ala Asp Arg Ala Arg Gly His Val Ala Glu Met Arg Asp Ala Leu Leu
545                 550                 555                 560

Thr Asp Gly Trp Asp Gly Ser Trp Phe Leu Arg Ala Tyr Asp Tyr Tyr
                565                 570                 575

Gly Asn Pro Ile Gly Thr Asp Ala His Asp Glu Gly Lys Ile Trp Ile
            580                 585                 590

Glu Pro Gln Gly Phe Ala Val Met Ala Gly Val Gly Val Gly Glu Gly
        595                 600                 605

Pro Gln Asp Thr Asp Ala Pro Ala Ile Lys Ala Leu Asp Ser Val Asn
    610                 615                 620

Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
```

```
                        645                 650                 655
Tyr Lys Glu Asn Gly Gly Ile Phe Cys His Ala Asn Pro Trp Val Ile
            660                 665                 670

Ile Ala Glu Thr Val Val Gly Arg Gly Gly Arg Ala Phe Asp Tyr Tyr
            675                 680                 685

Lys Arg Ile Thr Pro Ala Tyr Arg Glu Asp Ile Ser Asp Val His Arg
            690                 695                 700

Leu Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
            740                 745                 750

Asp Gly Leu Val Val Asp Pro Gln Ile Gly Pro Asp Val Pro Ser Phe
            755                 760                 765

Thr Val Thr Arg Val Ala Arg Gly Ala Thr Tyr Glu Ile Thr Val Thr
            770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820
```

<210> SEQ ID NO 4
<211> LENGTH: 822
<212> TYPE: PRT
<213> ORGANISM: Artificial Sequence
<220> FEATURE:
<223> OTHER INFORMATION: Mutant sequence 3

<400> SEQUENCE: 4

```
Met Arg Tyr Gly His Phe Asp Asp Glu Ala Arg Glu Tyr Val Ile Thr
1               5                   10                  15

Thr Pro His Thr Pro Tyr Pro Trp Ile Asn Tyr Leu Gly Ser Glu Gln
            20                  25                  30

Phe Phe Ser Leu Leu Ser His Gln Ala Gly Gly Tyr Ser Phe Tyr Arg
        35                  40                  45

Asp Ala Lys Met Arg Arg Leu Thr Arg Tyr Tyr Asn Asn Ile Pro
    50                  55                  60

Ala Asp Ala Gly Gly Arg Tyr Leu Tyr Val Asn Asp Gly Gly Asp Val
65                  70                  75                  80

Trp Thr Pro Ser Trp Leu Pro Val Lys Ala Asp Leu Asp His Phe Glu
                85                  90                  95

Ala Arg His Gly Leu Gly Tyr Ser Thr Ile Thr Gly Glu Arg Asn Gly
            100                 105                 110

Val Arg Val Glu Thr Leu Phe Phe Val Pro Val Gly Glu Asn Ala Glu
        115                 120                 125

Val Gln Lys Val Thr Val Thr Asn Thr Ser Asp Ser Tyr Lys Ser Leu
    130                 135                 140

Thr Leu Phe Ser Phe Val Glu Phe Cys Leu Trp Asn Ala Gln Asp Asp
145                 150                 155                 160

Gln Thr Asn Tyr Gln Arg Asn Leu Ser Ile Gly Glu Val Glu Val Glu
                165                 170                 175

Gln Glu Ser Pro His Gly Ser Ala Ile Tyr His Arg Thr Glu Tyr Arg
            180                 185                 190
```

```
Glu Arg Arg Asp His Tyr Ala Val Phe Ala Val Asn Thr Gln Ala Glu
            195                 200                 205
Gly Phe Asp Thr Asp Arg Asp Thr Phe Val Gly Ala Tyr Asn Ser Leu
            210                 215                 220
Gly Glu Ala Ala Val Pro Leu Lys Gly Glu Ser Ala Asn Ser Val Ala
225                 230                 235                 240
Ser Gly Trp Tyr Pro Ile Gly Ser His Ser Val Ala Val Ser Leu Ala
            245                 250                 255
Pro Gly Glu Ser Arg Glu Leu Val Tyr Val Leu Gly Tyr Val Glu Asn
            260                 265                 270
Pro Asp Glu Glu Lys Trp Ala Asp Ala Lys Gln Val Val Asn Lys
            275                 280                 285
Glu Arg Ala His Ala Leu Leu Ser Arg Phe Ala Thr Ser Glu Gln Thr
            290                 295                 300
Asp Ala Ala Phe Ala Ala Leu Lys Asp Tyr Trp Thr Asp Leu Leu Ser
305                 310                 315                 320
Thr Tyr Ser Val Ser Ser Asn Asp Glu Lys Leu Asp Arg Met Val Asn
            325                 330                 335
Ile Trp Asn Gln Tyr Gln Cys Met Val Thr Phe Asn Met Ser Arg Ser
            340                 345                 350
Ala Ser Phe Phe Glu Thr Gly Ile Gly Arg Gly Met Gly Phe Arg Asp
            355                 360                 365
Ser Asn Gln Asp Leu Leu Gly Phe Val His Leu Ile Pro Glu Arg Ala
            370                 375                 380
Arg Glu Arg Ile Ile Asp Ile Ala Ser Thr Gln Phe Arg Asp Gly Ser
385                 390                 395                 400
Ala Tyr His Gln Tyr Gln Pro Leu Thr Lys Arg Gly Asn Asn Asp Ile
            405                 410                 415
Gly Ser Gly Phe Asn Asp Asp Pro Leu Trp Leu Ile Ala Gly Thr Ala
            420                 425                 430
Ala Tyr Ile Lys Glu Thr Gly Asp Phe Ser Ile Leu Asp Glu Pro Val
            435                 440                 445
Pro Phe Asp Asn Glu Pro Gly Ser Glu Val Pro Leu Phe Glu His Leu
            450                 455                 460
Thr Arg Ser Phe Glu Phe Thr Val Thr His Arg Gly Pro His Gly Leu
465                 470                 475                 480
Pro Leu Ile Gly Arg Ala Asp Trp Asn Asp Cys Leu Asn Leu Asn Cys
            485                 490                 495
Phe Ser Thr Thr Pro Gly Glu Ser Phe Gln Thr Ile Glu Asn Gln Ala
            500                 505                 510
Gly Gly Val Ala Glu Ser Thr Phe Ile Ala Ala Gln Phe Val Leu Tyr
            515                 520                 525
Gly Glu Gln Tyr Ala Glu Leu Ala Ala Arg Arg Gly Leu Ala Asp Val
            530                 535                 540
Ala Asp Arg Ala Arg Gly His Val Ala Glu Met Arg Asp Ala Leu Leu
545                 550                 555                 560
Thr Asp Gly Trp Asp Gly Ser Trp Phe Leu Arg Ala Tyr Asp Tyr Tyr
            565                 570                 575
Gly Asn Pro Ile Gly Thr Asp Ala His Asp Glu Gly Lys Ile Trp Ile
            580                 585                 590
Glu Pro Gln Gly Phe Ala Val Met Ala Gly Val Gly Val Gly Glu Gly
            595                 600                 605
Pro Gln Asp Thr Asp Ala Pro Ala Ile Lys Ala Leu Asp Ser Val Asn
```

```
            610                 615                 620
Glu Met Leu Ala Thr Asp His Gly Met Val Leu Gln Tyr Pro Ala Tyr
625                 630                 635                 640

Thr Thr Tyr Gln Val His Met Gly Glu Val Ser Thr Tyr Pro Pro Gly
                645                 650                 655

Tyr Lys Glu Asn Gly Gly Ile Phe Cys His Ala Asn Pro Trp Val Ile
                660                 665                 670

Ile Ala Glu Thr Val Val Gly Arg Gly Arg Ala Phe Asp Tyr Tyr
                675                 680                 685

Lys Arg Ile Thr Pro Ala Tyr Arg Glu Asp Ile Ser Asp Val His Arg
            690                 695                 700

Leu Glu Pro Tyr Val Tyr Ala Gln Met Ile Ala Gly Lys Glu Ala Val
705                 710                 715                 720

Arg His Gly Glu Ala Lys Asn Ser Trp Leu Thr Gly Thr Ala Ala Trp
                725                 730                 735

Asn Phe Val Thr Val Ser Gln Tyr Leu Leu Gly Val Arg Pro Glu Tyr
                740                 745                 750

Asp Gly Leu Val Val Asp Pro Gln Ile Gly Pro Asp Val Pro Ser Phe
                755                 760                 765

Thr Val Thr Arg Val Ala Arg Gly Ala Thr Tyr Glu Ile Thr Val Thr
            770                 775                 780

Asn Ser Gly Thr Asp Gly Ser Arg Gly Arg Leu Val Val Asp Gly Thr
785                 790                 795                 800

Pro Val Glu Gly Asn Leu Val Pro Tyr Ala Pro Ala Gly Ser Thr Val
                805                 810                 815

Arg Val Asp Val Thr Leu
            820

<210> SEQ ID NO 5
<211> LENGTH: 2469
<212> TYPE: DNA
<213> ORGANISM: Cellvibrio gilvus

<400> SEQUENCE: 5
atgcggtacg gccatttcga cgacgcggcg cgcgagtacg tcatcacgac gcctcacacc      60
ccctacccgt ggatcaacta cctcgggtcg gagcagttct tctcgctgct ctcccaccag     120
gccggcggct actcgttcta ccgcgacgcc aagatgcggc ggctcacgcg ctaccgctac     180
aacaacatcc ccgcggacgc gggcggccgg tacctgtacg tcaacgacgg cggcgacgtg     240
tggaccccgt cgtggctgcc ggtcaaggcg gacctggacc acttcgaggc gcgccacggc     300
ctcggctact cgcgcatcac gggcgagcgc aacggcctga aggtcgagac gctcttcttc     360
gtcccgctcg gcgagaacgc cgaggtgcag aaggtcaccg tcaccaacac gtccgacgcc     420
ccgaagacgg cgacgctgtt ctcgttcgtc gagttctgcc tgtggaacgc gcaggacgac     480
cagacgaact accagcgcaa cctgtcgatc ggcgaggtcg aggtcgagca ggacggcccg     540
cacggctcgg cgatctacca caagaccgag taccgcgagc gccgcgacca ctacgccgtg     600
ttcggcgtga acacccgcgc ggacggcttc gacacggacc gcgacacgtt cgtgggcgcg     660
tacaactcgc tggcgagggc gtccgtcccg cgcgccggga agtccgcgga ctcggtcgcg     720
tcgggctggt acccgatcgg ctcgcactcc gtcgccgtga cgctgcagcc cggcgagtcc     780
cgcgacctcg tctacgtgct gggctacctg gagaacccccg acgaggagaa gtgggccgac     840
gacgcccacc aggtcgtcaa caaggcgccc gcgcacgcgc tgctgggccg gttcgcgacg     900
agcgagcagg tcgacgccgc cctggaggcg ctgaactcct actggacgaa cctgctctcg     960
```

```
acgtactcgg tgtcgagcac cgacgagaag ctcgaccgga tggtcaacat ctggaaccag    1020
taccagtgca tggtcacgtt caacatgtcg cgctcggcgt cgttcttcga cgcgggcatc    1080
ggccgcggga tgggcttccg cgactccaac caggacctcc tgggcttcgt gcacctgatc    1140
ccggagcgcg cgcgcgagcg gatcatcgac atcgcctcga cgcagttcgc ggacggctcg    1200
gcgtaccacc agtaccagcc gctcacgaag cgcgggaaca acgacatcgg ctcgggcttc    1260
aacgacgacc cgctgtggct catcgcgggc gtggcggcgt acatcaagga gtccggcgac    1320
tggggcatcc tcgacgagcc cgtgccgttc gacaacgagc ccggctccga ggtcccgctg    1380
ttcgagcacc tgacgcgctc cttccagttc acggtgcaga accgcggccc gcacggcctg    1440
ccgctcatcg gccgtgccga ctggaacgac tgcctcaacc tcaactgctt ctcgacgacc    1500
ccgggcgagt cgttccagac gaccgagaac caggcggggcg cgtcgcgga gtccgtgttc    1560 atcgcggcgc agttcgtgct ctacggcgcg gagtacgcca cgctcgcgga gcgtcgcggc    1620
ctcgcggacg tcgccaccga ggcgcgcaag tacgtcgacg aggtgcgtgc cgcggtgctc    1680
gagcacggct gggacggcca gtggttcctg cgtgcctacg actactacgg caacccggtc    1740
ggcacggacg ccaagcccga gggcaagatc tggatcgagc gcagggcttt cgccgtcatg    1800
gcgggcatcg gcgtcggcga gggcccggac gacgcggacg cgccggccgt caaggcgctc    1860
gactccgtga acgagatgct cggcacgccg cacggcctgg tgctgcagta cccggcgtac    1920
acgacgtacc agatcgagct cggcgaggtc tccacgtacc cgcccggcta caaggagaac    1980
ggcggcatct tctgccacaa caaccccctgg gtgatcatcg ccgagacggt cgtggggcgc    2040
ggtgcgcagg cgttcgacta ctacaagcgg atcacccccg cgtaccgcga ggacatctcc    2100
gacacgcaca gctcgagcc gtacgtgtac gcgcagatga tcgcgggcaa ggaggcggtg    2160
cgcgccggcg aggcgaagaa ctcgtggctc accggaacgg cggcgtggaa cttcgtcgcg    2220
gtgtcccagt acctgctggg cgtgcggccc gactacgacg gcctcgtggt cgacccgcag    2280
atcggtccgg acgtcccctc gtacacggtc acccgcgtgg cccgcggcgc gacgtacgag    2340
atcacggtga ccaactcggg cgccccgggc gcgcgtgcgt cgctcacggt cgacggcgcg    2400
cccgtcgacg gccgcacggt cccctacgcc ccggccggct cgaccgtccg cgtcgaggtg    2460
accgtctga                                                          2469
```

<210> SEQ ID NO 6
<211> LENGTH: 23
<212> TYPE: DNA
<213> ORGANISM: Artificial
<220> FEATURE:
<223> OTHER INFORMATION: Forward primer
<400> SEQUENCE: 6

```
aacgttacgg gcacttcgac gac                                             23
```

<210> SEQ ID NO 7
<211> LENGTH: 29
<212> TYPE: DNA
<213> ORGANISM: Artificial
<220> FEATURE:
<223> OTHER INFORMATION: Reverse primer
<400> SEQUENCE: 7

```
attctgcagc tagagggtca cgtcgacgc                                       29
```

<210> SEQ ID NO 8
<211> LENGTH: 22

```
<212> TYPE: DNA
<213> ORGANISM: Artificial
<220> FEATURE:
<223> OTHER INFORMATION: CPmutF1 primer

<400> SEQUENCE: 8
cgttcgtcgg cgcgtacaac tc                                          22

<210> SEQ ID NO 9
<211> LENGTH: 21
<212> TYPE: DNA
<213> ORGANISM: Artificial
<220> FEATURE:
<223> OTHER INFORMATION: CPmutR1 primer

<400> SEQUENCE: 9
acgacgagcc cgtcgtactc c                                           21

<210> SEQ ID NO 10
<211> LENGTH: 50
<212> TYPE: DNA
<213> ORGANISM: Artificial Sequence
<220> FEATURE:
<223> OTHER INFORMATION: Primer

<400> SEQUENCE: 10
caggaaacag accatgcacc atcaccatca ccatcgttac gggcacttcg            50
```

LACTOSE PHOSPHORYLASE ENZYMES

CROSS-REFERENCE TO RELATED APPLICATIONS

This is a national phase entry under 35 U.S.C. §371 of International Patent Application PCT/EP2008/068076, filed Dec. 19, 2008, published in English as International Patent Publication WO 2009/080774 A1 on Jul. 2, 2009, which claims the benefit under Article 8 of the Patent Cooperation Treaty to European Patent Application Serial No. 07150211.6, filed Dec. 20, 2007, the entire disclosure of each of which is hereby incorporated herein by this reference.

TECHNICAL FIELD

The present invention relates to novel lactose phosphorylase enzymes and the uses thereof. More specifically, the invention relates to lactose phosphorylase enzymes created by mutation of a cellobiose phosphorylase from *Cellulomonas uda*. By introducing mutations in this enzyme, the activity can be switched from cellobiose phosphorylase into lactose phosphorylase.

BACKGROUND

Monosaccharides that carry an α-linked phosphate group are key intermediates in the Leloir pathway for the synthesis of glycosidic linkages. Indeed, they can be converted into nucleotide sugars that are donor substrates for glycosyltransferases. In vivo, galactose-1-phosphate is converted into UDP-galactose by galactose-1-phosphate uridyl transferase (GALT). Absence of this enzyme results in the accumulation of toxic levels of galactose in the blood, a genetic disorder known as galactosemia (Fridovich-Keil, 2006). UDP-galactose, in turn, is the substrate for galactosyltransferases that are involved in the synthesis of a wide variety of important carbohydrate epitopes in glycoproteins and glycolipids (Varki, 1993).

Glycosyl phosphates have traditionally been synthesized by means of conventional chemical catalysis. Starting in 1937, several procedures using different catalysts and different glycosyl or phosphate donors have been described in the literature (Cori et al., 1937; MacDonald, 1961; Inage et al., 1982; Schmidt et al., 1982; Sim et al., 1993). More information can be found in patent EP0553297: "The preparation of glycosyl phosphate triesters." Chemical phosphorylation of carbohydrates typically consists of multistep reaction schemes, resulting in a low overall yield, and is not very successful in achieving anomeric selectivity. The development of an enzymatic phosphorylation technology is consequently highly desirable, and has the additional benefit of reducing the amount of waste that is generated in the process (green chemistry).

Enzymes that phosphorylate monosaccharides belong to the class of kinases (phosphotransferases), which require ATP as phosphate donor. Most of these sugar kinases phosphorylate their substrate at the C6 position and not at the anomeric center. The only known exceptions are galactokinase (EC 2.7.1.6) that produces α-D-galactose-1-phosphate, and fucokinase (EC 2.7.1.52) that produces β-L-fucose-1-phosphate. Interestingly, the specificity of galactokinase has been broadened by means of directed evolution to include D-talose and L-glucose as substrates (Hoffmeister et al., 2003), and a patent describing the use of such galactokinase variants has been published: "Sugar kinases with expanded substrate specificity and their use" (WO2005056786). Although a kinase is available for the production of α-D-galactose-1-phosphate, the need for the unstable and expensive ATP as a phosphate donor is a serious drawback for industrial applications.

In spite of their name, glycoside phosphorylases do not actually phosphorylate their substrate but, instead, catalyze the phosphorolysis of di- and polysaccharides to produce phosphorylated monosaccharides. These enzymes are highly attractive as biocatalysts because they only require anorganic phosphate as donor, and have long been used for the production of α-D-glucose-1-phosphate from maltodextrin (Griessler et al., 1996) or sucrose (Goedl et al., 2007). More information can be found in U.S. Pat. No. 6,764,841: "Production process of glucose-1-phosphate." Unfortunately, the specificity of carbohydrate phosphorylases is very limited and only one enzyme is known to produce α-D-galactose-1-phosphate in Nature, i.e., the lacto-N-biose phosphorylase found in Bifidobacteria (Kitaoka et al., 2005). Lacto-N-biose I or β-D-galactosyl-(1,3)-N-acetyl-D-glucosamine is a structural component of oligosaccharides present only in human milk and is not easy to obtain in large quantities (Nishimoto and Kitaoka, 2007).

Japanese Patent No. 9224691 discloses the production of sugar phosphate, useful as food material, by reacting chitobiose or lactose with phosphoric acid in the presence of cellobiose phosphorylase from *Cellvibrio gilvus*. Starting from lactose, α-D-galactose-1-phosphate is obtained. However, this is only a side activity of the cellobiose phosphorylase, and both long reaction times (48 hours) and the rather low yield make this enzyme, although scientifically interesting, unsuitable for an industrial use.

DISCLOSURE

Surprisingly, we found that the cellobiose phosphorylase from *Cellulomonas uda* also shows an activity towards lactose, with the production of α-D-galactose-1-phosphate. Even more surprisingly, mutants could be obtained with a strongly increased lactose phosphorylase activity. The mutants do have a specific activity that is at least ten times higher, preferably about 50 times higher, than the specific activity of wild-type *Cellvibrio gilvus*.

A first aspect of the invention is a lactose phosphorylase enzyme with a specific activity of at least 0.05 units/mg, preferably at least 0.1 units/mg, more preferably 0.2 units/mg, even more preferably at least 0.25 units/mg, as measured on 200 mM lactose in 50 mM MES-buffer pH 6.6 at 37° C. One unit (U) is defined as the amount of enzyme that converts 1 µmole of substrate in 1 minute under these conditions.

Preferably, the lactose phosphorylase enzyme is obtained by mutation of a cellobiose phosphorylase. Preferably, the mutation is situated in the region 300-750, even more preferably, in one of the regions 335-375, 395-435, 475-515 and 640-680 of the *Cellulomonas uda* sequence, or in an equivalent region of a homologous enzyme. A "homologous enzyme," as used herein, is an enzyme with cellobiose phosphorylase activity, and at least 40% identity, preferably 50% identity, more preferably 60% identity, more preferably 70% identity, even more preferably 80% identity, and most preferably 90% identity with the *Cellulomonas uda* sequence, as measured in a BLAST alignment (Tatusova and Madden, 1999). An "equivalent region," as used herein, means that the region can be identified by an alignment of both sequences, on the base of the conserved residues, by a BLAST alignment (Tatusova and Madden, 1999). Preferably, the lactose phosphorylase is obtained by mutation of the cellobiose phosphorylase of *Cellulomonas uda*. More preferably, the lactose phosphorylase enzyme comprises at least the mutation A397 and/or the mutation T508 and/or the mutation N667 of SEQ ID NO:1 (*C. uda* enzyme) or the equivalent mutation in a homologous enzyme, even more preferably, the mutations are selected from the group consisting of A397R, T508A, T508I, N667T and N667A, even more preferably, the enzyme comprises SEQ ID NO:2 (mutant sequence 1), SEQ ID NO:3 (mutant sequence 2) or SEQ ID NO:4 (mutant sequence 3). In one preferred embodiment, the enzyme consists of SEQ ID NO:2. In another preferred embodiment, the enzyme consists of SEQ ID NO:3. In still another preferred embodiment, the enzyme consists of SEQ ID NO:4.

Another aspect of the invention is a nucleic acid sequence encoding a lactose phosphorylase enzyme according to the invention. A "nucleic acid," as used herein, includes, but is not limited to, a DNA sequence, a cDNA sequence or an RNA sequence. Such a nucleic acid sequence can be used, as a non-limiting example, for overproduction of the enzyme in a homologous host organism or for heterologous production of the enzyme in an organism other than *Cellulomonas uda*.

Another aspect of the invention is a mutant cellobiose phosphorylase enzyme, with increased lactose phosphorylase activity compared to the wild-type enzyme. Lactose phosphorylase activity is measured as described in materials and methods to the examples; preferably, the activity is expressed as specific activity. Preferably, the lactose phosphorylase activity is increased by at least a factor 3, more preferably, by at least a factor 5, even more preferably, by at least a factor 7, and most preferably, by at least a factor 10, compared to the wild-type activity. A "mutant enzyme," as used herein, is an enzyme whereby at least one amino acid residue is replaced, deleted and/or inserted in the wild-type sequence. Preferably, the mutation is an amino acid replacement, even more preferably, the mutation is a replacement of at least two amino acids, and most preferably, it is a replacement of at least three amino acids.

Another aspect of the invention is the use of a lactose phosphorylase enzyme according to the invention for the production of galactose-1-phosphate. Still another aspect of the invention is the use of a lactose phosphorylase enzyme according to the invention for the production of lactose.

DETAILED DESCRIPTION OF THE INVENTION

EXAMPLES

Materials and Methods to the Examples
Bacterial Strains, Plasmids and Growth Conditions The cellobiose phosphorylase gene (accession number AY343322) was cloned from *Cellulomonas uda* DSM20108. The organism was grown in Tryptone Soya Broth medium (TSB: 17 g/L tryptone, 3 g/L papaic digest of soybean meal, 2.5 g/L glucose, 2.5 g/L $K_2HPO_4$, 5 g/L NaCl) at 30° C. The pGEM-T plasmid (Promega) was used for cloning of the PCR fragments and was stored in *E. coli* DH5α. The pTrc99A plasmid (4177 bp, containing the IPTG-inducible trc promoter and an ampicillin resistance gene) was used for construction of the cellobiose phosphorylase expression vector. Ultracompetent *Escherichia coli* XL10-Gold cells (Stratagene) (TetrD(mcrA)183 D(mcrCB-hsdSMR-mrr)173 endA1 supE44 thi-1 recA1 gyrA96 relA1 lac Hte [F' proAB lacI$^q$ZDM15 Tn10 (Tetr) Amy Cam$^r$]), were used for transformation with variant libraries. For plasmid isolation, *E. coli* was routinely grown overnight at 37° C. in LB medium (10 g/L tryptone, 5 g/L yeast extract, 5 g/L NaCl, pH 7.0) supplemented with 100 mg/L ampicillin. For expression of recombinant cellobiose phosphorylase, the growth medium was supplemented with isopropyl-β-D-thiogalactoside (IPTG) to a final concentration of 0.1 mM. *E. coli* cells expressing improved enzyme variants were selected in minimal lactose medium (pH 7.4) composed of M9 salts (6 g/L $Na_2HPO_4$, 3 g/L $KH_2PO_4$, 1 g/L $NH_4Cl$, 0.5 g/L NaCl), 20 mg/L proline, 0.1 mM $CaCl_2.2H_2O$, 1 mM $MgSO_4$, 1 mM thiamine-HCl, 18 μM $FeCl_2.4H_2O$, 6.9 μM $ZnCl_2$, 100 mg/L ampicillin, 0.1 mM IPTG and 1% (w/v) lactose.

Construction of the Cellobiose Phosphorylase Expression Vector

*C. uda* was grown in TSB medium for 16 hours, after which genomic DNA was extracted with the GenElute Bacterial Genomic DNA kit (Sigma). The cellobiose phosphorylase gene was amplified from the genomic DNA using the High Fidelity PCR Master kit (Roche) with primers containing restriction sites:

```
forward primer
5'-AACGTTACGGGCACTTCGACGAC-3';       (SEQ ID NO: 6)

reverse primer
5'-ATTCTGCAGCTAGAGGGTCACGTCGACGC-3'. (SEQ ID NO: 7)
```

The Psp1406I and PstI restriction sites are underlined in the forward and reverse primers, respectively. DMSO was added to a final concentration of 5% to improve amplification from the GC-rich template. The following PCR cycling conditions were used: 95° C. (10 minutes); 35 cycles of 94° C. (1 minute), 62° C. (1 minute) and 72° C. (3 minutes); 72° C. (7 minutes). A 2477 bp fragment containing the full-length cellobiose phosphorylase gene was thus obtained and ligated into the pGEM-T vector. The resulting plasmid was named pGCP and was used to construct an expression vector for cellobiose phosphorylase. After digestion of 5.3 μg of the pGCP plasmid with 10 units of Psp14061 (Roche) restriction enzyme, the 3531 bp fragment was blunted with 3 units of Klenow polymerase (Roche). The resulting fragment was cut with 10 units of PstI restriction enzyme and the 2467 by used for ligation with the expression vector. 3.1 μg of the pTrc99A expression vector was cut with 10 units of NcoI and the restriction fragment was blunted with 3 units of Klenow polymerase. The resulting fragment was cut with PstI and the 4132 bp fragment used for ligation with the 2467 bp fragment containing the cellobiose phosphorylase gene. The ligation reaction consisted of 63 ng of the 2467 by fragment, 44 ng of the 4132 bp fragment, 5 units T4 DNA polymerase (Fermentas) and 5% PEG4000. After overnight incubation at 22° C., *E. coli* was transformed with the ligation mixture and plated on LB medium supplemented with ampicillin. The cellobiose phosphorylase expression vector obtained after plasmid extraction was named pXCP.

Mutagenesis Methods

Random mutagenesis of the cellobiose phosphorylase gene was performed with the GeneMorph II EZClone Domain Mutagenesis Kit (Stratagene) according to the manufacturer's instructions. Forty nanograms of the pXCP expression vector was used as template and error-prone PCR was performed with the following PCR primers:

```
                                         (SEQ ID NO: 8)
5'-CGTTCGTCGGCGCGTACAACTC-3'   (CPmutF1, forward)

(SEQ ID NO: 9)
5'-ACGACGAGCCCGTCGTACTCC-3'    (CPmutR1, reverse).
```

DMSO (1% final concentration) was added to the PCR reaction mixture to improve amplification from the GC-rich template. PCR cycling conditions were as follows: 95° C. (2 minutes); 35 cycles of 95° C. (45 seconds), 65° C. (45 seconds) and 72° C. (2 minutes); 72° C. (10 minutes). The 1624 bp PCR fragment was gel-purified and used for the so-called EZClone reaction in which the mutated genes are cloned into the pXCP expression vector by whole-plasmid PCR. The purified PCR fragment was used as megaprimer (500 ng) and wild-type pXCP vector (50 ng) as template. PCR cycling conditions were as follows: 95° C. (1 minute); 30 cycles of 95° C. (50 seconds), 60° C. (50 seconds) and 68° C. (14 minutes). After the reaction, 10 units of DpnI restriction enzyme were added to the reaction mixture and incubated overnight at 37° C. to completely digest parental template DNA. The DpnI-treated PCR mixture was transformed into E. coli XL10-Gold and the transformation mixture was plated on LB medium containing ampicillin. Several colonies were picked and sequenced to determine the mutagenesis rate.

Site-directed and site-saturation mutagenesis was performed with the QuikChange Multi Site-Directed Mutagenesis Kit (Stratagene) according to the manufacturer's instructions. The primers contained the appropriate codon for mutagenesis (NNS for saturation), and PCR cycling conditions were as follows: 95° C. (3 minutes); 30 cycles of 95° C. (1 minute), 55° C. (1 minute) and 65° C. (14 minutes). After the reaction, 10 units of DpnI restriction enzyme were added to the reaction mixture and incubated overnight at 37° C. to completely digest parental template DNA. The PCR mixture was transformed into E. coli XL10-Gold and the transformation mixture was plated on LB medium containing ampicillin. Several colonies were picked and sequenced to identify the mutated plasmids.

Selection for Lactose Phosphorylase Enzyme Variants

The mutant DNA library was transformed into E. coli XL10-Gold cells and the transformation mixture inoculated in 20 mL LB medium supplemented with 100 mg/L ampicillin. After six hours of growth, IPTG (0.1 mM final concentration) and lactose (1% final concentration) were added and the culture was grown for another 16 hours at 30° C. The culture was then washed with phosphate buffered saline (PBS, 8 g/L NaCl, 0.2 g/L KCl, 1.44 g/L $Na_2HPO_4$, 0.25 g/L $KH_2PO_4$; pH 7.4) and inoculated (0.25%) in 50 mL lactose minimal medium supplemented with ampicillin and IPTG. The selection culture was grown at 37° C. to an $OD_{600}$ of about 1, after which a fresh selection culture was started by inoculation (2%) of the grown culture in 20 mL lactose minimal medium supplemented with ampicillin and IPTG. After four such cycles, an aliquot of the culture was plated on LB medium supplemented with ampicillin. Several colonies were picked and sequenced to identify the mutations.

Screening for Lactose Phosphorylase Enzyme Variants

The mutant DNA library was transformed into E. coli XL10-Gold cells and the transformation mixture was plated on LB medium containing ampicillin. Colonies were picked with an automated colony-picker (QPix2, Genetix) and inoculated into 96-well flat-bottomed microtiter plates containing 175 µL LB medium per well, supplemented with ampicillin. The microtiter plates were incubated for 16 hours at 37° C. and 250 rpm. Recombinant enzyme expression was then induced by inoculation of the grown mini-cultures into new microtiter plates containing 175 µL LB medium per well, supplemented with ampicillin and 0.1 mM IPTG. After incubation for 16 hours at 37° C. and 250 rpm, the microtiter plates were centrifuged at 2500 rpm for 10 minutes, and the pellets frozen at −20° C. The pellets were lysed with 100 µL of lysis buffer composed of 50 mM Tris-HCl (pH 7.5), 1 mM EDTA, 0.5% TRITON X-100® (nonionic surfactant), 4 mM $MgCl_2$, 50 mM NaCl and 1 mg/mL lysozyme. Lysis was carried out for 30 minutes at 37° C. on a liquid handling robot (Freedom EVO 200, Tecan). After lysis, the plates were centrifuged at 3500 rpm for 10 minutes and the supernatants (crude cell extracts) were used for enzyme screening. Enzyme reactions were carried out at 37° C. in microtiter plates by mixing 30 µL crude cell extract with 170 µL substrate solution (200 mM lactose and 30 mM $KH_2PO_4$ in 50 mM Mes-buffer pH 6.6). After 1 hour incubation, 50 µL samples were taken to determine the amount of released glucose via the glucose oxidase/peroxidase assay (Trinder, 1969).

Enzymatic Characterization

For a thorough characterization of the wild-type enzyme or improved variant, the corresponding expression vector was used to transform E. coli XL10-Gold and the resulting transformant was picked and grown at 37° C. in LB medium supplemented with ampicillin. Expression of the recombinant enzyme was induced by adding IPTG to a final concentration of 0.1 mM when the optical density at 600 nm of the culture reached 0.6. After six hours of induction, the culture was centrifuged for 10 minutes at 15000 g and the pellet was frozen at −20° C. Crude cell extracts were prepared using the EasyLyse Bacterial Protein Extraction Solution (Epicentre). These cell extracts contain the phosphorylase enzyme that was used in an assay, either directly or in a purified form.

The purification was performed in 50 mM Tris-HCl buffer pH 7.5 with equipment from GE Healthcare, and consisted of a combination of anion-exchange (Q-SEPHAROSE FAST-FLOW® (crosslinked polysaccharide polymer), 100-500 mM NaCl), gelfiltration (Superdex200, 300 mM NaCl) and hydrophobic interaction chromatography (OCTYL SEPHAROSE® (crosslinked polysaccharide polymer), 10 mM NaCl and 2.5% ammoniumsulphate).

Enzyme reactions were performed using 30 mM $KH_2PO_4$ and either 30 mM cellobiose or 200 mM lactose in 50 mM MES-buffer pH 6.6 at 37° C. At regular intervals, samples were inactivated by boiling for five minutes and the released glucose was measured via the glucose oxidase/peroxidase assay (Trinder, 1969). One unit (U) of enzyme activity was defined as the amount of enzyme that converts 1 µmole of substrate in one minute under these conditions.

Cloning and Purification of his-Tagged Enzyme

For simplifying the purification, a His6-tag was inserted in the pXCP-vector between the first and second codon by means of PCR (using the primer sequence 5'-caggaaacagac-catgcaccatcaccatcaccatcgttacgggcacttcg-3' (SEQ ID NO:10)) with the QuikChange XL site-directed mutagenesis kit from Stratagene (La Jolla, Calif., USA). The variant enzymes were cloned into this vector by conventional cloning procedures. The enzymes were purified with the IMAC QuickPick kit from Bio-Nobile Oy (Turku, Finland) according to the manufacturer's instructions.

Example 1

Expression and Characterization of the Wild-Type Cellobiose Phosphorylase

A cellobiose phosphorylase expression vector (pXCP) was successfully constructed by ligation of the cellobiose phosphorylase gene from Cellulomonas uda into a pTrc99A expression plasmid, as described in the materials and methods section. After transformation of E. coli XL10-Gold and induction, crude cell extracts were prepared by cell lysis and centrifugation. An activity of about 5 U and 0.02 U per mL of cell extract was obtained on 30 mM cellobiose and 200 mM lactose, respectively (pH 6.6 and 37° C.).

The wild-type enzyme was purified to electrophoretic homogeneity by a combination of chromatographic techniques. The first step was anion-exchange chromatography, in which the enzyme eluted with a salt concentration of 500 mM. Subsequent gelfiltration yielded an enzyme sample that was almost completely pure. Hydrophobic interaction chromatography was used as a final step, in which the enzyme did not bind to the column but eluted with 2.5% ammoniumsulphate. A specific activity of 12.66 U/mg and 0.0406 U/mg was obtained on 30 mM cellobiose and 200 mM lactose, respectively (pH 6.6 and 37° C.).

Example 2

Development of a Lactose Phosphorylase by Random Mutagenesis

The pXCP plasmid was used as template for random mutagenesis of the cellobiose phosphorylase gene via error-prone PCR. Using structural information from the homologous *Cellvibrio gilvus* cellobiose phosphorylase (Hidaka et al., 2006; PDB 2CQT), we restricted random mutagenesis to the residues between T216 and V757. This resulted in the amplification of a 1624 by DNA fragment that was cloned into the pXCP expression plasmid. The generated DNA library was used to transform *E. coli* XL10-Gold, which was plated on LB medium containing ampicillin to determine the mutation frequency of the library. An average mutation frequency of 6.5 DNA mutations per 1000 by was obtained.

In order to find enzyme variants with improved lactose phosphorylase activity, an in vivo selection system was developed. Since *E. coli* XL10-Gold does not express a β-galactosidase, only the cells that are transformed with an active lactose phosphorylase should be able to grow in minimal medium with lactose as the sole carbon source. Moreover, the cells expressing the highest lactose phosphorylase activity will grow fastest, meaning that the best enzyme present in the library can be selected using an enrichment culture. We performed four cycles of growth in lactose minimal medium and plated an aliquot of the culture on LB medium. Three colonies were picked and grown for plasmid extraction. Sequencing of the plasmids revealed that they all contained the same mutations, meaning that one variant was indeed enriched in the selection culture and this variant was called LP1. Nine DNA mutations were identified and these resulted in six amino acid substitutions (Table 1).

TABLE 1

Overview of mutations found in the LP1 variant obtained after selection

| DNA mutation | Amino acid substitution | Distance to donor (Å)* |
|---|---|---|
| g735a | — | — |
| g930a | — | — |
| c1190t | A397V | 23.7 |
| c1410t | — | — |
| a1522g | T508A | 17.1 |
| g1534a | A512T | 22.9 |
| g1669a | D557N | 26.5 |
| a2000c | N667T | 9.6 |
| g2041a | G681S | 26.8 |

*Distance from the Cα atom of the amino acid to the C1 atom of glycerol in the 3D structure of the homologous *C. gilvus* cellobiose phosphorylase (PDB 2CQT)

After enzyme production and extraction, a five-fold increase in lactose phosphorylase activity could be detected for the LP1 variant while the cellobiose phosphorylase activity had decreased four-fold compared to the wild-type enzyme (Table 2). We investigated the importance of each amino acid substitution in the LP1 variant by reverting it to the wild-type amino acid. These experiments revealed that only T508A and N667T contribute to the improved activity on lactose. Interestingly, two of the other mutations were found to have a negative effect on lactose phosphorylase activity: A397V and G681S. Based on these results, we constructed the double mutant T508A/N667T, which was called LP2 and has about two times more lactose phosphorylase activity than the parent LP1 variant. The results are summarized in Table 2(a).

TABLE 2

Activity of the recombinant enzymes (wild-type and mutants) in crude cell extracts (a), and as his-tagged purified enzyme (b)

(a)

| Activity (U/mL cell extract) | cellobiose | lactose |
|---|---|---|
| WT | 5.42 ± 0.31 | 0.020 ± 0.002 |
| LP1 | 1.34 ± 0.21 | 0.098 ± 0.006 |
| LP2 | 1.63 ± 0.27 | 0.217 ± 0.007 |
| LP3 | 2.16 ± 0.23 | 0.298 ± 0.006 |

(b)

| Activity (U/mg pure enzyme) | cellobiose | lactose |
|---|---|---|
| WT | 7.78 ± 0.34 | 0.033 ± 0.003 |
| LP1 | 1.35 ± 0.11 | 0.100 ± 0.008 |
| LP2 | 1.71 ± 0.13 | 0.171 ± 0.014 |
| LP3 | 2.61 ± 0.21 | 0.249 ± 0.017 |

A His6-tag was inserted before the start codon of the genes, and the enzymes were purified with the IMAC QuickPick kit from Bio-Nobile Oy (Turku, Finland) according to the manufacturer's instructions. The specific activity of the pure his tagged enzymes were measured on 200 mM lactose, in 30 mM KH$_2$PO$_4$-50 mM MES buffer, pH 6.6, at 37° C. The specific activity of the LP2 double mutant was 0.171 units/mg, as compared with 0.033 units/mg for the purified *C. uda* wild-type enzyme (Table 2(b)). Activities on cellobiose are given as comparison.

The two mutant positions were at random mutated into any other amino acid, and the resulting combinations were screened on activity. One variant, T508I/N667A (indicated as LP3) showed about 50% higher activity than the LP2 variant, as measured both on crude extract (Table 2(a)) as on purified enzyme (Table 2(b)).

Example 3

Comparison of the Activity of the Mutant *Cellulomonas uda* Enzyme with the Activity of *Cellvibrio gilvus*

The gene coding for the cellobiose phosphorylase from *C. gilvus* (SEQ ID NO:5) was synthesized by Genscript (Piscataway, N.J., USA). The cloning, expression, mutagenesis, extraction and measurement of the enzymatic activity was performed as described for enzyme from *Cellulomonas uda*. The results are summarized in Table 3.

TABLE 3 analysis of the activity of cellobiose phosphorylase of
Cellvibrio gilvus (wt and T508I mutant) on cellobiose and lactose

| activity (U/mg crude extract) | cellobiose | lactose |
| --- | --- | --- |
| Wild-type | 1.046 ± 0.052 | 0.0036 ± 0.0001 |
| T508I | 0.699 ± 0.029 | 0.0044 ± 0.0002 |
| N667A | 0.891 ± 0.027 | 0.0041 ± 0.0002 |
| T508I + N667A | 0.529 ± 0.020 | 0.0050 ± 0.0003 |

In order to evaluate the effect of mutations at positions T508 and N667 (equivalent of the position T508, respectively, the position N667 in *Cellulomonas uda*) of the *Cellvibrio gilvus* enzyme, the T at position 508 was replaced by I, and the N at position 667 was replaced by A in a similar way as described for *Cellulomonas uda*. Similar to what was noticed in *Cellulomonas uda*, introducing a mutation at these positions increased the activity, but the resulting activity for both the mutations and for the double mutation was still significantly lower than was obtained for *Cellulomonas uda*.

Example 4

Optimization of the Lactose Phosphorylase Activity

The wild-type cellobiose phosphorylase from *Cellulomonas uda* displays little activity on 200 mM lactose at pH 6.6 and 37° C. (although far higher than the activity measured for *Cellvibrio gilvus*). The lactose phosphorylase activity has already been increased ten-fold by introducing the mutations N667T and T508A, but additional enzyme engineering will further improve the efficiency of the production of α-D-galactose-1-phosphate.

Libraries of variant enzymes are produced by both random mutagenesis and site-saturation mutagenesis, as described in the materials and methods section. For the random mutagenesis, epPCR followed by selection in lactose minimal medium is used. For the site-saturation mutagenesis, active-site residues are targeted and the effect is evaluated by high-throughput screening. Variants with increased lactose phosphorylase activity are sequenced and the individual effect of all identified mutations is determined by means of site-directed mutagenesis. The beneficial mutations are pooled into one enzyme that is used as a starting point for a new round of directed evolution.

Example 5

Application of the Improved Enzyme Variants in Production Process

The best enzyme variant at the end of each cycle of directed evolution is produced at a larger scale and characterized more thoroughly. Its specific activity on 200 mM lactose and 30 mM phosphate in 50 mM MES buffer pH 6.6 at 37° C. is determined. Furthermore, its kinetic parameters and the optimal substrate concentration for maximal efficiency of α-D-galactose-1-phosphate production are determined. Because the cellobiose phosphorylase from *Cellvibrio gilvus* has been reported to be moderately active on lactose, a comparative analysis is performed with the improved enzyme variants. In those experiments, the test conditions described in Japanese Patent No. 9224691 are used: mixing 2 U/ml of enzyme with 10 mM lactose and 10 mM phosphate in Tris/HCL-buffer pH 7. After 48 hours of reaction at 37° C., 1.5 mM of α-galactose-1-phosphate was produced with the enzyme of *Cellvibrio gilvus*.

Because the phosphorolysis of disaccharides constitutes a reversible reaction, a lactose phosphorylase is also useful for the enzymatic synthesis of lactose from α-galactose-1-phosphate and glucose. Such lactose is very interesting for the manufacture of pharmaceutical formulations since it is not derived from animal sources, and hence guaranteed BSE-free. The synthetic capacities of our improved variants are tested by mixing enzyme with substrate, inactivating samples at regular intervals by boiling for five minutes, and measuring the lactose concentration by means of HPLC. The specific activity on 200 mM α-D-galactose-1-phosphate and 30 mM glucose in 50 mM MES-buffer pH 6.6 at 37° C. is determined, as well as the kinetic parameters and the optimal substrate concentration for maximal efficiency of lactose production.

Example 6

Because residue 397 clearly influences the lactose phosphorylase activity of the LP1-variant (albeit negatively in the case of the mutation A397V), we decided to saturate this position in the LP3-variant. After screening one microtiter plate (96 colonies), we could indeed identify a variant with increased activity on lactose. This enzyme contains the mutation A397R and has a specific activity of 0.177±0.007 U/mg crude cell extract, compared to 0.161±0.006 U/mg crude cell extract for the LP3-variant.

REFERENCES

Cori C. F., S. P. Colowick and G. T. Cori (1937). The isolation and synthesis of glucose-1-phosphoric acid. *J. Biol. Chem.* 121, 465-477.

Fridovich-Keil J. L. (2006). Galactosemia: the good, the bad, and the unknown. *J. Cell. Physiol.* 209, 701-705.

Goedl C., A. Schwarz, A. Minani and B. Nidetzky (2007). Recombinant sucrose phosphorylase from *Leuconostoc mesenteroides*: Characterization, kinetic studies of trans-glucosylation, and application of immobilized enzyme for production of α-D-glucose 1-phosphate. *J. Biotechnol.* 129, 77-86.

Griessler R., A. Weinhäusel, D. Haltrich, K. D. Kulbe and B. Nidetzky (1996). Optimization of glucose-1-phosphate production employing glucan-phosphorylases in continuous enzyme membrane reactors. *Ann. N.Y. Acad. Sci.* 799, 494-500.

Hidaka M., M. Kitaoka, K. Hayashi, T. Wakagi, H. Shoun and S. Fushinobu (2006). Structural dissection of the reaction mechanism of cellobiose phosphorylase. *Biochem. J.* 398, 37-43.

Hoffmeister D., J. Yang, L. Liu and J. S. Thorson (2003). Creation of the first anomeric D/L-sugar kinase by means of directed evolution. *Procl. Natl. Acad. Sci.* 110, 13184-13189.

Inage M, H. Chaki, S. Kusumoto and T. Shiba (1982). A convenient preparative method of carbohydrate phosphates with butyllithium and phosphorochloridate. *Chem. Lett.* 8, 1281-1284.

Kitaoka M., J. Tian and M. Nishimoto (2005). Novel putative galactose operon involving Lacto-N-biose phosphorylase in *Bifidobacterium longum*. *Appl. Environ. Microbiol.* 71, 3158-3162.

MacDonald D. L. (1961). A new route to glycosyl phosphates. *J. Org. Chem.* 27, 1107-1109.

Nishimoto M. and M. Kitaoka (2007). Practical preparation of Lacto-N-biose I, a candidate for the Bifidus factor in human milk. *Biosci. Biotechnol. Biochem.* 71, 2101-2104.

Schmidt R. R., M. Stumpp and J. Michel (1982). Alpha-D-glucopyranosyl and beta-D-glucopyranosyl phosphates from O-alpha-D-glucopyranosyl trichloroacetimidates. *Tetrahedron Lett.* 23, 405-408.

Sim M. M., H. Kondo and C. H. Wong (1993). Synthesis and use of glycosyl phosphites: an effective route to glycosyl phosphates, sugar nucleotides and glycosides. *J. Am. Chem. Soc.* 115, 2260-2267.

Tatusova T. A. and T. L. Madden (1999). BLAST 2 sequences—a new tool for comparing protein and nucleotide sequences. *FEMS Microbiol. Lett.* 174, 247-250.

Trinder P. (1969). Measurement of serum glucose. *Ann. Clin. Biochem.* 6, 24-26.

Varki A. (1993). Biological roles of oligosaccharides: all of the theories are correct. *Glycobiology* 3, 97-130.

---

The invention claimed is:

1. An isolated lactose phosphorylase enzyme, wherein the lactose phosphorylase enzyme comprises at least mutation T508 and/or N667 of SEQ ID NO:1, and has a specific activity of at least 0.05 Unit/mg, as may be determined under conditions of 200 mM lactose in 50 mM MES-buffer pH 6.6 at 37° C., wherein one Unit is an amount of enzyme needed to convert 1 µmole of substrate in 1 minute under said conditions.

2. The isolated lactose phosphorylase enzyme of claim 1, further comprising at least one mutation selected from the group consisting of T508A, T508I, N667T and N667A of SEQ ID NO:1.

3. The isolated lactose phosphorylase enzyme of claim 2, comprising SEQ ID NO:2.

4. The isolated lactose phosphorylase enzyme of claim 2, comprising SEQ ID NO:3.

5. The isolated lactose phosphorylase enzyme of claim 2, comprising SEQ ID NO:4.

6. A process for producing the lactose phosphorylase enzyme according to claim 1, the method comprising:
   expressing a nucleic acid molecule encoding the lactose phosphorylase enzyme in a cell, and
   recovering the lactose phosphorylase enzyme thus expressed.

7. A process for producing galactose-1-phosphate, the improvement comprising:
   utilizing the lactose phosphorylase enzyme of claim 1, for the production of galactose-1-phosphate.

8. A process for producing lactose, the improvement comprising:
   utilizing the lactose phosphorylase enzyme of claim 1, for the production of lactose.

* * * * *